United States Patent [19]

Ohta et al.

[11] 4,449,677

[45] May 22, 1984

[54] TAPE CASSETTE

[75] Inventors: Shuichi Ohta, Fujima; Atsuhiro Kumagai, Yokohama, both of Japan

[73] Assignee: Sony Corporation, Tokyo, Japan

[21] Appl. No.: 390,983

[22] Filed: Jun. 22, 1982

[30] Foreign Application Priority Data

Jun. 22, 1981 [JP] Japan .................. 56-96246

[51] Int. Cl.³ .................. G03B 1/04; G11B 15/32; G11B 23/04
[52] U.S. Cl. .................. 242/199; 360/132
[58] Field of Search .............. 242/192, 194, 197–200, 242/204; 360/93, 96.1, 96.5, 132; 354/72–78

[56] References Cited

U.S. PATENT DOCUMENTS

| 4,004,752 | 1/1977 | Kamaya | 242/198 |
| 4,021,006 | 5/1977 | Morimoto et al. | 242/199 |
| 4,173,319 | 11/1979 | Umeda | 242/199 |
| 4,249,710 | 2/1981 | Dobbs et al. | 242/199 |
| 4,358,070 | 11/1982 | Okamura et al. | 242/197 |
| 4,386,746 | 6/1983 | Okamura et al. | 242/199 |

Primary Examiner—Leonard D. Christian
Attorney, Agent, or Firm—Lewis H. Eslinger; Alvin Sinderbrand

[57] ABSTRACT

A tape cassette with tape reels mounted therewithin having an opening portion formed in one side of the tape cassette and a notched portion formed in the lower surface of the cassette in a position adjacent to the opening portion, wherein a tape wound round the tape reels is passed along the opening portion, characterized by the combination therewith of an improved construction comprising a front cover capable of being opened and closed which covers the front face of the tape passed along the opening portion and an inner cover capable of being opened and closed which covers the back of the tape in an opposed relation to the front cover, whereby the tape is enclosed while being held from before and behind between the front cover and the inner cover and consequently the adhesion of dust or the like to the tape and the damage of the tape can be prevented.

11 Claims, 15 Drawing Figures

TAPE CASSETTE

BACKGROUND OF THE INVENTION

(1) Field of the Invention

This invention relates to a tape cassette suitable for application to such magnetic recording/reproducing apparatus as video tape recorders, various other magnetic recording/reproducing type information processors and the like.

(2) Description of the Prior Art

In a tape cassette for video tape recorders, as well known, an opening portion is formed in one side thereof and a notched portion adjacent to this opening portion is formed in the lower surface of the cassette. By loading this tape cassette onto the body of a video tape recorder, a tape loading guide is inserted from the notched portion into the inside of the tape in the cassette, and thereafter by moving the tape loading guide from the opening portion to the exterior of the cassette, the tape is drawn out on the cassette and loaded onto a predetermined tape travelling path.

Conventional tape cassettes of this sort have been constructed in such a manner that a pivotable cover is mounted in front of the aforementioned opening portion to prevent the tape from accidentally jumping out of the cassette from the opening portion and thereby being damaged, and when the tape cassette is loaded onto the body of a video tape recorder, the pivotable cover is pivotally opened.

However, such conventional tape cassettes have been disadvantageous in that because of no consideration given to the prevention of entry of dust or the like into the cassette interior through the foregoing notched portion, the dust or the like once entered the cassette interior adheres to the magnetic surface of the tape, thus resulting in that drop-out is apt to occur at the time of recording or reproducing. Moreover, the tape which has been passed along the opening portion is apt to be loosened due to vibration or the like at the time of cassette loading or carrying, and when inserting the tape loading guide into the notched portion, its guide head and the tape may strike against each other thereby causing damage of the tape accidentally.

SUMMARY OF THE INVENTION

It is an object of the present invention to provide a tape cassette wherein a tape passed along an opening portion formed in one side of the tape cassette is enclosed between a front cover capable of being opened and closed and an inner cover, thereby preventing dust or the like from adhering to the tape or the tape user's finger or the like from contacting or damaging the tape.

It is another object of the present invention to provide a tape cassette capable of preventing the tape from becoming loose within the aforesaid opening portion even when the tape cassette undergoes vibration or the like, and when loading the cassette to a video tape recorder or the like, preventing a tape loading guide, which is inserted from a notched portion formed in the lower surface of the tape cassette into the inside of the above opening portion, from striking against the tape and damaging the latter.

In accordance with one aspect of the present invention a tape cassette comprises a housing containing reels on which a supply of tape is wound and having an opening along one side of the housing and a cutout communicating with the opening along a portion of the opening, the tape being guided between the reels in a path extending along the opening. A front cover is mounted on the housing for movement relative thereto between a closed position for covering the opening in front of the tape and an opened position for exposing the opening and the front of the tape. An inner cover, movable with the front cover, is positioned behind the tape, to enclose the tape between the front cover and the inner cover, when the front cover is in its closed position. When the front cover is in its opened position, the back of the tape is exposed so that the tape can be engaged through the cutout for withdrawal of the tape through the opening.

In accordance with another aspect of the present invention, the tape cassette includes a reel locking means for preventing rotation of the reels in a direction that will loosen the tape in the opening. The reel locking means includes locking members for releasably engaging the reels to prevent rotation in that direction. The reel locking means is releasable by unlocking means on an apparatus that accepts the cassette when the cassette is inserted into the apparatus.

BRIEF DESCRIPTION OF THE DRAWINGS

The accompanying drawings illustrate an embodiment of the present invention applied to a tape cassette for a video tape recorder, in which.

DESCRIPTION OF A PREFERRED EMBODIMENT

An embodiment of the present invention applied to a tape cassette for a video tape recorder will be described herein-under with reference to the drawings.

Figure 1:
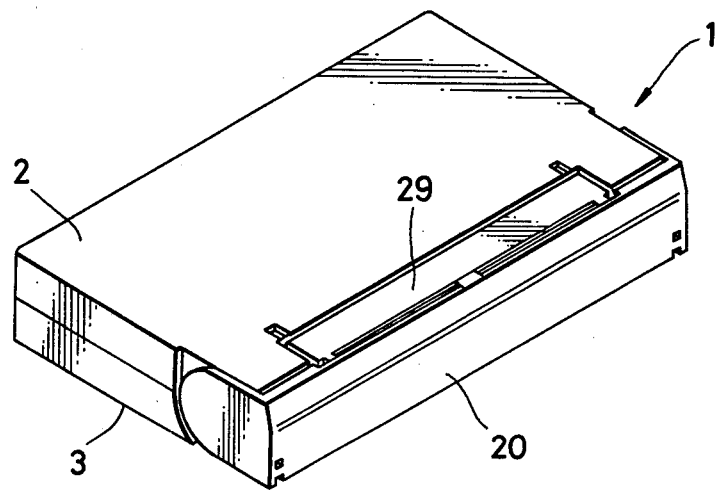
FIG. 1 is a perspective view of an external appearance of the tape cassette not loaded yet to the body of the video tape recorder.
Figure 2:
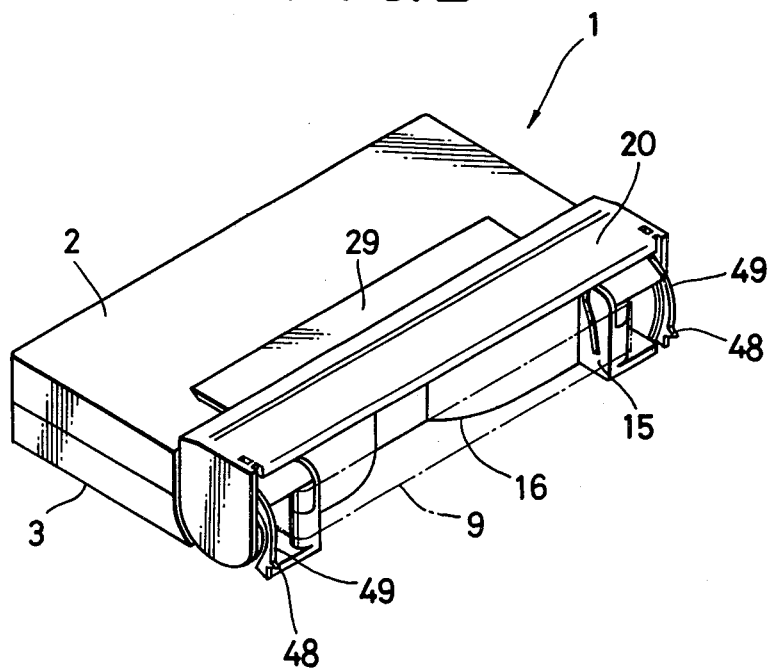
FIG. 2 is a perspective view of an external appearance of the tape cassette loaded to the body of the video tape recorder.
Figure 3:
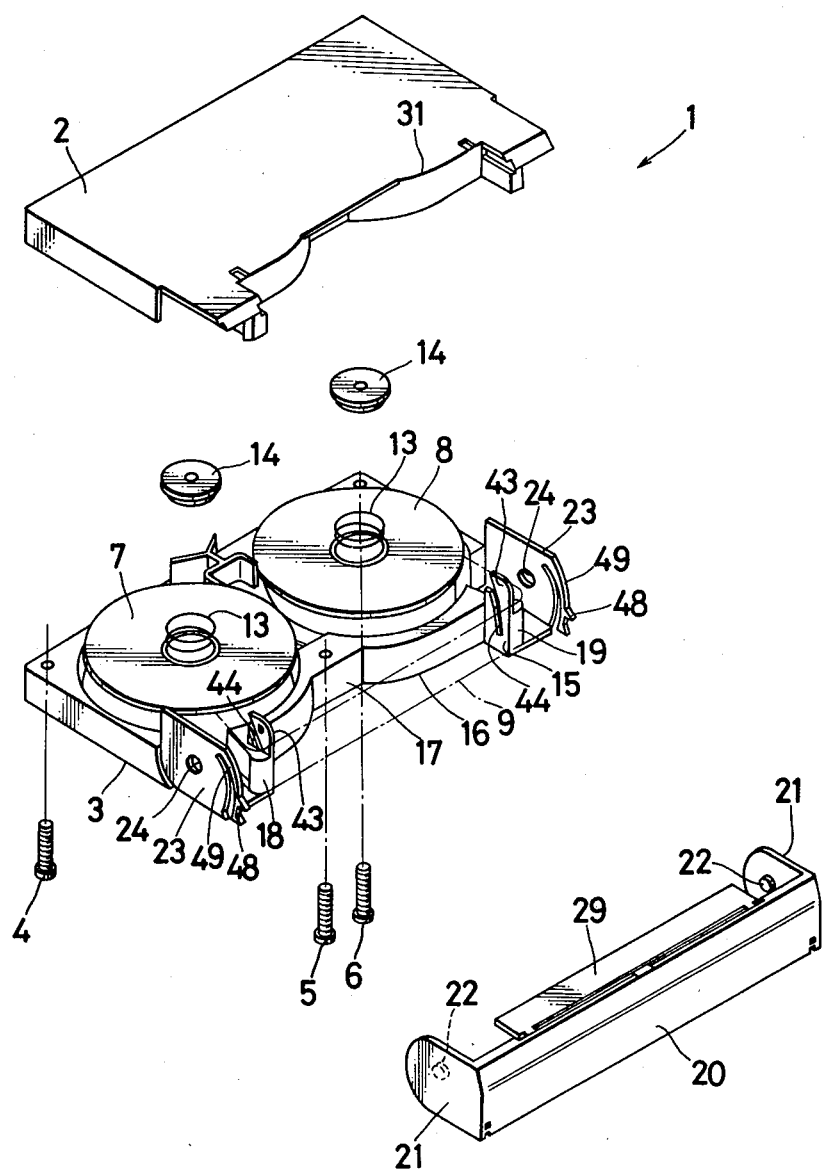
FIG. 3 is an exploded perspective view of the tape cassette.
Figure 6:
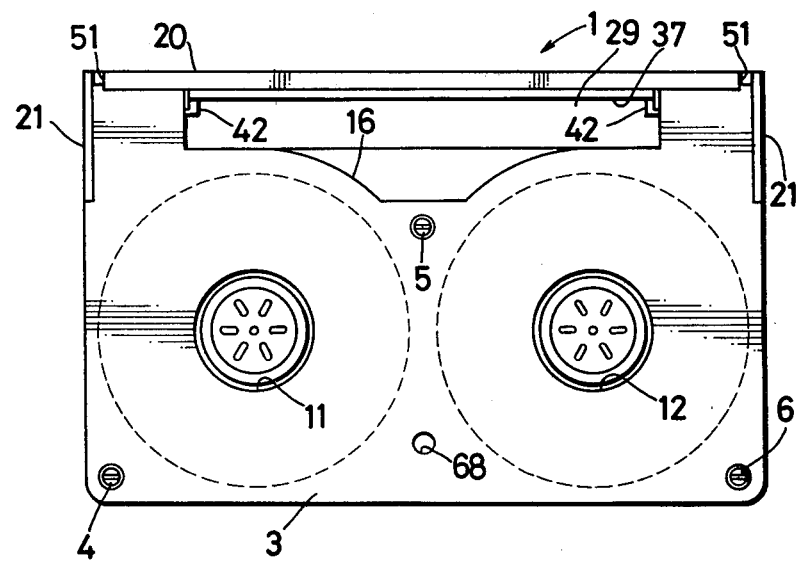
FIG. 6 is a rear view thereof.
Figure 14:
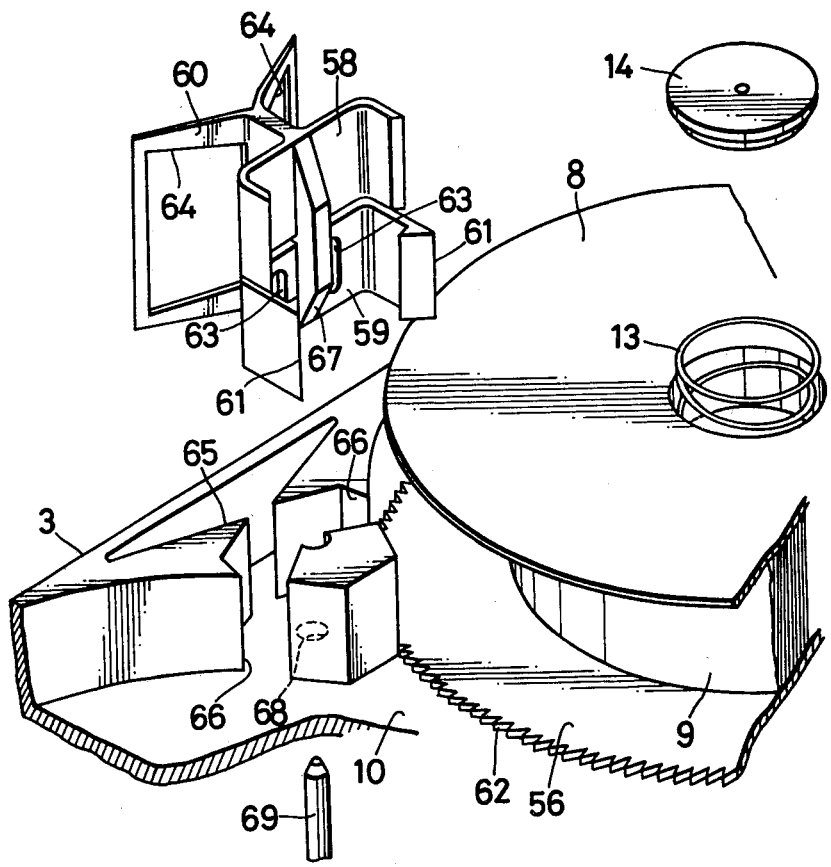
FIG. 14 is an exploded perspective view thereof.

Referring first to FIGS. 1 through 3, there is shown a tape cassette 1 which is constructed of an upper half 2 and a lower half 3 both molded from synthetic resin. The upper half 2 and the lower half 3 are fitted together from a vertical direction and fixed with set-screws 4 through 6 to form an integral housing with a top, or first, wall and a bottom, or second, wall. Within the tape cassette 1 is rotatably mounted a pair of tape reels 7 and 8, and a magnetic tape 9 (hereinafter referred to simply as the "tape") is wound round the tape reels 7 and 8. As shown in FIG. 14, the tape reels 7 and 8 are placed on a bottom partition 10 of the lower half 3, and as shown in FIG. 6, they are positioned by being fitted in a pair of reel insertion holes 11 and 12 formed in the bottom partition 10. In FIG. 3, the reference numeral 13 designates a pair of tape reel presser springs and numeral 14 designates a pair of caps applied to upper end portions of the presser springs 13.

In the front face or side of the tape cassette 1, as shown in FIG. 2, an opening portion or opening 15 is formed nearly throughout the full width of the cassette, while in the bottom partition 10 of the lower half 3 there is formed a notched portion or cutout 16 adjacent to the opening portion 15 as is shown in FIGS. 2, 3 and 6. At an edge portion of the notched portion 16, as shown in FIGS. 2 and 3, there is formed a vertical partition 17 which extends perpendicularly upward from the above edge portion and joins to the upper half 2, whereby the notched portion 16 and the interior of the tape casette 1 are separated each other. At both right and left end portions of the vertical partition 17 there are formed a pair of tape guide portions 18 and 19 whereby the tape 9 is guided and passed along the opening portion 15.

Figure 4:
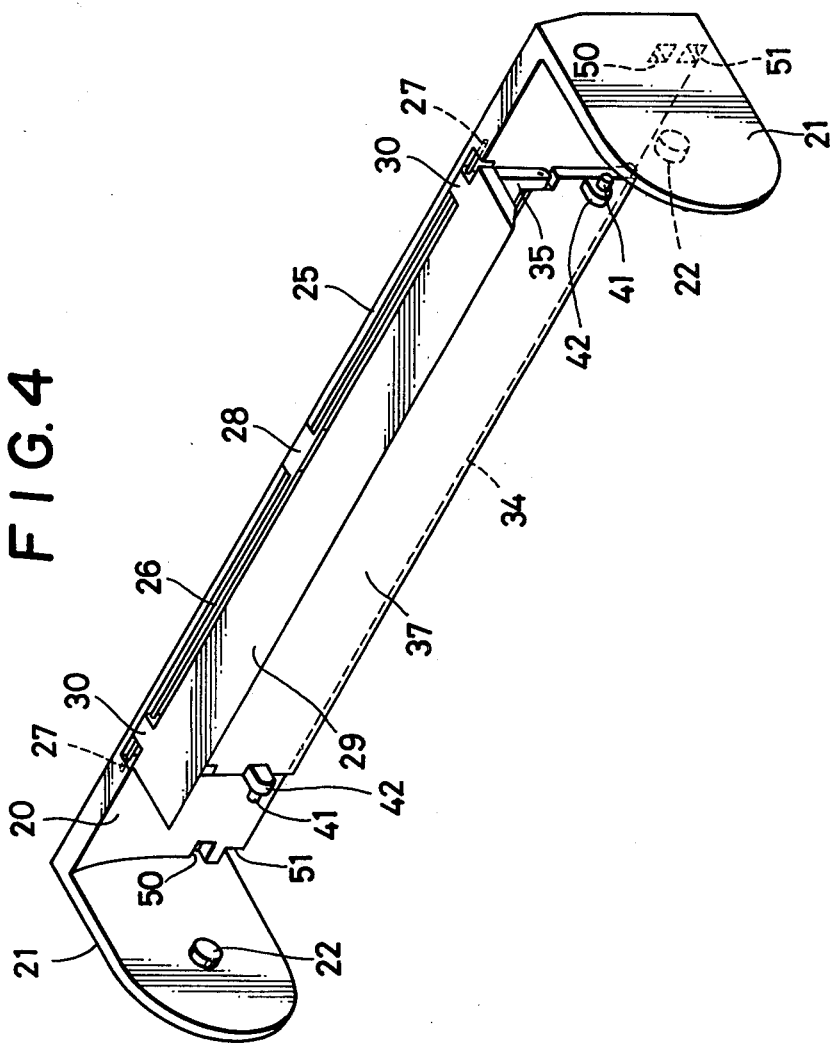
FIG. 4 is an enlarged perspective view of a front cover portion of the tape cassette.

As shown in FIGS. 3 and 4, the opening portion 15 is covered with a generally ]-shaped front cover 20, and in the insides of right and left end portions or cars 21 of the front cover 20 are integrally formed a pair of pivot pins 22. On the other hand, formed in both right and left end portions 23 of the opening portion 15 belonging to the lower half 3 are a pair of holes 24, in which are fitted the pivot pins 22 whereby the front cover 20 is made pivotable in the vertical direction. A torsion bar 26 molded from plastic material is disposed along an upper end portion 25 of the front cover 20 as is shown in FIG. 4. Both right and left end portions 27 of the torsion bar 26 are pivotable attached to the upper end portion 25 of the front cover 20, and its central portion 28 is fixed to the upper end portion 25 of the front cover 20. In the vicinities of the right and left and portions 27 are fixed the right and left end portions 30 of an upper or cutout cover 29 to the torsion bar 26. The upper cover 29 is arranged to cover an upper notched portion or the cutout 31 at an upper edge of the vertical partition 17 so as to get a good appearance. Thus, the notched portions 16 and 31 form a cutout that extends between and through the first and second walls of the cassette housing along a portion of the opening 15. As shown in FIGS. 2 through 9, when the front cover 20 is pivoted upwardly the upper cover 29 slides on the upper wall of the upper half 2 toward the back of the upper notched portion 31. Consequently, when the front cover 20 pivots upward, the torsion bar 26 is twisted and acts as a resilient torsion spring means to urge the upper cover 29 pivotally in a counterclockwise direction in FIG. 9, and by virtue of the reaction force, the front cover 20 is urged in a clockwise direction in FIG. 9 to its closed position. As mentioned above, the upper cover 29 is provided for the sake of good appearance that the upper notched portion 31 may not be seen directly. Therefore it is not always necessary from a functional standpoint of the tape cassette 1. That is, if there is provided some means else to urge pivotally the front cover 20 normally in a clockwise direction in FIG. 9, then functionally the upper cover 29 becomes no longer necessary. For example, this urging means may be of a construction such that a torsion spring is attached to one or both sides of the pair of pivot pins 22.

Figure 7:
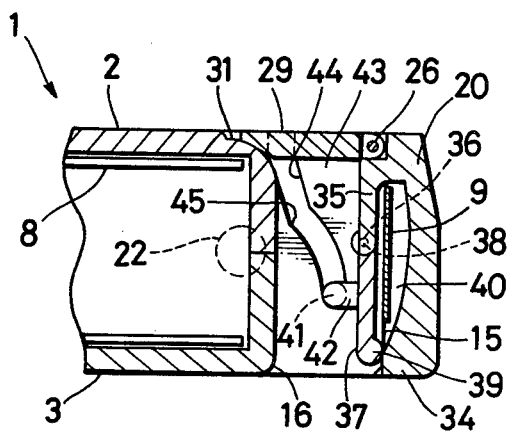
FIG. 7 is a sectional view taken on line VII—VII of FIG. 5.
Figure 8:
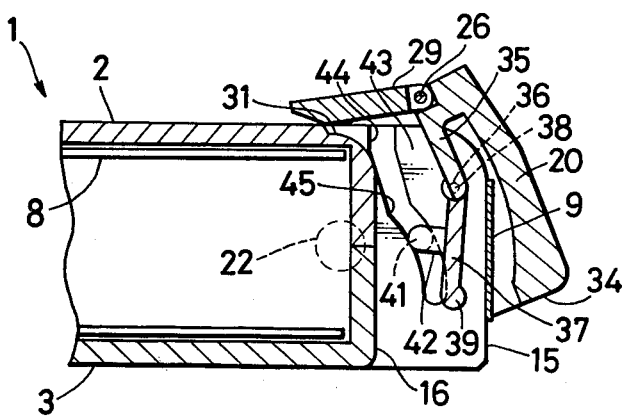
FIGS. 8 and 9 illustrate opening and closing operations of a tape cassette cover.
Figure 9:
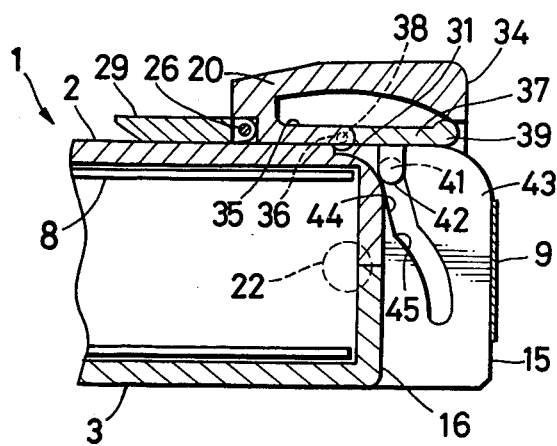

As shown in FIGS. 4 and 7 through 9, formed from the upper end portion 25 of the front cover 20 downward to the side of a lower end portion 34 is an inner plate 35 which covers nearly an upper half of the back of the front cover 20. A pair of holes 36 are formed in both right and left end portions of the lower end of the inner plate 35, and a pair of pivot pins 38 formed at both right and left end portions of the upper end of an inner cover 37 are fitted in the holes 36. That is, the inner cover 37 may turn freely on the pivot pins 38, and as shown in FIG. 7, in a pivoted position, in which the lower end portion 39 of the inner cover 37 contacts with the inside of the lower end portion 34 of the front cover 20, there is formed a tape chamber 40 partitioned with the inner plate 35 and the inner cover 37 on the backside of the front cover 20. The tape is thus enclosed between the inner cover and the front cover. As shown in FIGS. 7 through 9, the lower end portion 39 of the inner cover 37 is rounded in section so that it may contact with the inside of the lower end portion 34 of the front cover 20 closely without leaving space.

As shown in FIGS. 4 and 7 through 9, a pair of guide pins 41 are provided at both right and left end portions of the inner cover 37. The guide pins 41 are attached to tip end portions of a pair of brackets 42 which project from nearly central parts of both right and left portions of the inner cover 37 toward the side opposite to the front cover 20, and the above guide pins 41 project horizontally toward the outside. On the other hand, as shown in FIGS. 7 through 9, a pair of guide grooves 44 facing on the notched portion 16 side are formed in both right and left side portions or inside walls 43 of the vertical partition 17 which stand face to face each other at the ends of the cutout. The guide grooves 44 are formed obliquely from rear upper portions (left upper portions in FIGS. 7 through 9) of the side portions 43 to front lower portions (right lower portions in the same figures) thereof, and central portions 45 of the guide grooves 44 are somewhat closer to the pivot pins 22. That is, the guide grooves 44 have a turned V-shaped form wherein the central portions 45 are the closest to the pivot pins 22. The guide pins 41 are inserted in the guide grooves 44, and when the front cover 20 is pivoted, the guide pins 41 are guided by the guide grooves 44 while being in sliding contact therewith. That is, in a completely closed state of the front cover 20 as is shown in FIG. 7, or in a completely opened state thereof as is shown in FIG. 9, the lower end portion 39 of the inner cover 37 contacts with the inside of the lower end portion 34 of the front cover 20. However, during opening or closing operation of the front cover 20, the guide pins 41 of the inner cover 37 approach the pivot pins 22 and the inner cover 37 pivots about the pivot pins 38.

Figure 10:
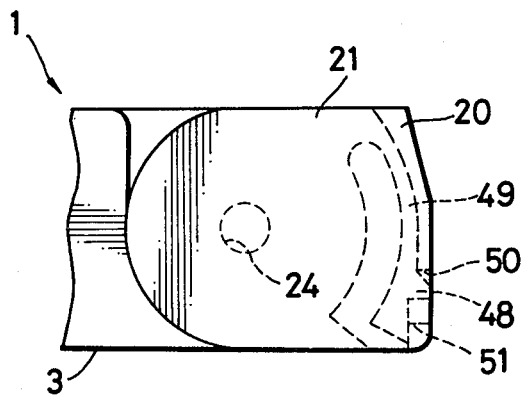
FIG. 10 is a partial side view of the tape cassette.
Figure 11:
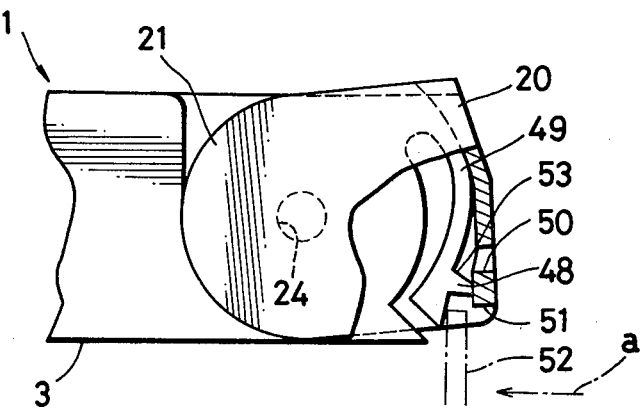
FIGS. 11 and 12 illustrate an unlocking state of the front cover.
Figure 12:
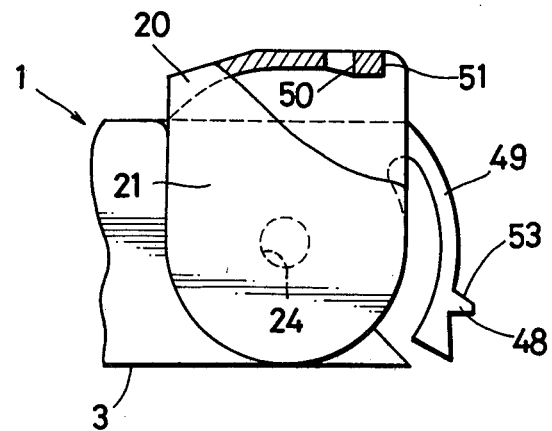

At the front edge parts of the right and left end portions 23 of the lower half 3 there are integrally formed a pair of locking pawls or latching means 48 as is shown in FIGS. 2, 3, 10 and 11. More particularly, the locking pawls 48 are formed at tip end portions of a pair of leaf spring portions 49 which project from the upper ends of both front edge parts of the end portion 23 toward the lower ends thereof, the locking pawls 48 being movable resiliently in the right and left direction in FIG. 12. On the other hand, as shown in FIG. 4, a pair of locking holes 50 are formed in lower ends of both right and left end portions of the front cover 20. When the front cover 20 is closed, as shown in FIG. 10, the locking pawls 48 are fitted in the locking holes 50 to lock the front cover 20 in the closed portion. The leaf spring portions 49 are arcuate around the pin holes 24 so as not to impede the opening and closing operation for the front cover 20. In a lower edge portion of the front cover 20 there are formed a pair of slits 51 just below the locking holes 50. When the front cover 20 is in a fully closed state, as shown in FIG. 10, the slits 51 are positioned just in front of the tip end parts of the leaf spring portions 49. When loading the tape cassette 1 onto a cassette holder, as shown in FIG. 11, a pair of projections 52 formed on the cassette holder are inserted through the slits 51 and act as unlatching means to urge the tip end parts of the leaf spring portions 49 to allow the locking pawls 48 to be disengaged or released from the locking holes 50. The locking pawls 48 have inclined portions 53 as is shown in FIGS. 11 and 12, and when closing the front cover 20 the inner walls of the slits 51 urge the inclined portion 53, so that the tip end portions of the leaf spring portions 49 are bent to the left as in the case of FIG. 11. That is, immediately thereafter, the locking pawls 48 and the locking holes 50 are clickwise engaged with each other by the restoring force of the leaf spring portions 49.

Figure 5:
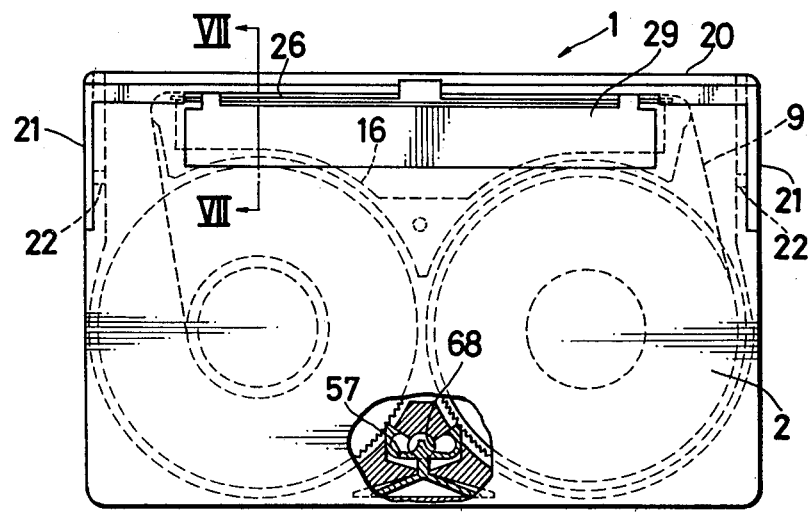
FIG. 5 is a plan view of the tape cassette.
Figure 13:
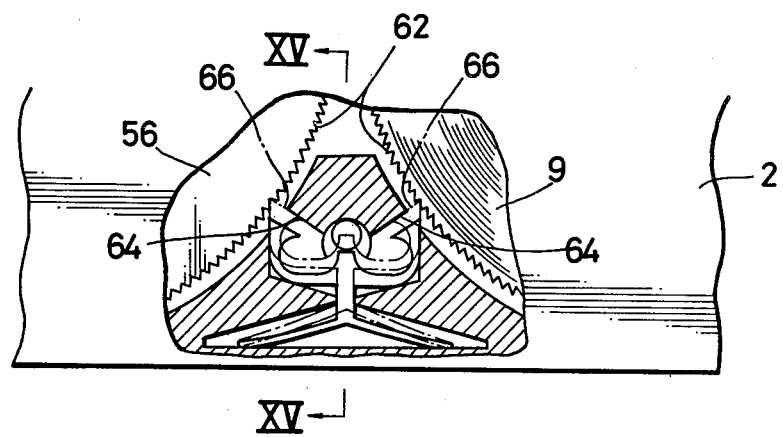
FIG. 13 is an enlarged plan view of a reel locking pawl portion shown in FIG. 5 in a loaded state of the tape cassette.

In the tape cassette 1, as shown in FIG. 5, there is arranged a reel locking pawl 57 between the tape reels 7 and 8. The reel locking pawl 57 is integrally molded from plastic material, and as shown in FIG. 14, it mainly comprises a first ]-shaped plate portion 59 and portion 58, a second ]-shaped plate wedge-like pawl portions 61. On the other hand, lower side plates 56 of the tape reels 7 and 8 are provided at the respective outer peripheral poritons with saw-toothed portions 62 as is shown in FIGS. 13 and 14, with which are engaged the pair of pawl portions 61 of the reel locking pawl 57 so that the rotation of the tape reels 7 and 8 in the tape slackening direction can be locked. That is, the pawl portions 61 of the reel locking pawl 57 mounted in the tape cassette 1 are made movable in the longitudinal direction (in the vertical direction in FIG. 13) by the resilience of the leaf spring portion 60, and normally (while the tape cassette 1 is not loaded) the pawl portions 61 are held in pressure engagement with the pair of toothed portion 62 by the urging force of the leaf spring portion 60. The second plate portion 59 and the leaf spring portion 60 are each provided with a pair of notched holes 63 and a pair of notched holes 64, respectively, whereby the portion 59 and 60 are given a moderate resilience. For loading the reel locking pawl 57 into the tape cassette 1, as shown in detail in FIG. 14, a pawl loading notch is formed in each of the upper and lower halves (in FIG. 14 there is shown only a pawl loading notch 65 of the lower half 3), when fitting together the upper and lower halves from above and below, the reel locking pawl 57 is loaded or fitted into those pawl loading notches. And as indicated with alternate long and short dash lines in FIG. 13, the pawl portion 61 are projected to the tape reels 7 and 8 side from a pair of right and left opening portions 66 of the pawl loading notch 65 of the lower half 3.

Figure 15:
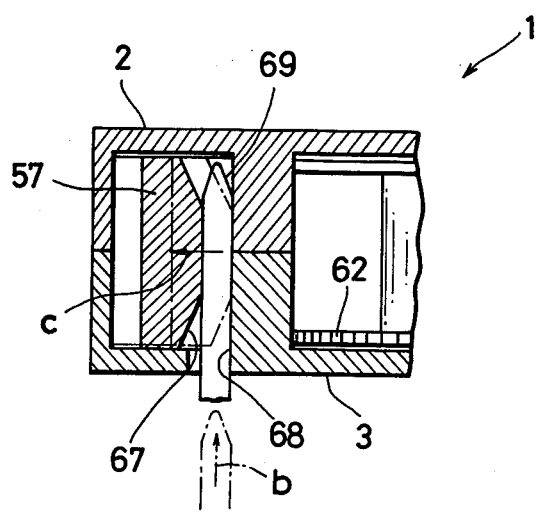
FIG. 15 is a sectional view taken on line XV—XV of FIG. 13.

At a central part of the second plate portion 59 of the reel locking pawl 57 there is formed an inclined surface 67 as is shown in FIGS. 14 and 15. On the other hand, in the bottom partition of the pawl loading notch 65 there is formed a pin hole 68 in a position just below the inclined surface 67. When loading the tape cassette 1, as shown in FIG. 15, an unlocking pin 69 is inserted through the hole 68 in the direction of arrow "b" and its tip end portion urges the inclined surface 67. That is, at the time of loading of the tape cassette 1, the first and second plate portions 58 and 59 move in the direction of arrow "c" in FIG. 15 together with the pawl portions 61 and thereby unlock the tape reels 7 and 8.

In the tape cassette 1 having the hereinabove described construction, normally as shown in FIG. 7, the front of the tape 9 passed along the opening portion 15 is covered with the front cover 20 and its back is covered with the inner plate 35 and the inner cover 37. That is, the tape 9 is enclosed in the tape chamber 40 while being put between the front cover 20 on the one hand and the inner plate 35 and inner cover 37 on the other. In this enclosed state, as shown in FIG. 10, the locking pawls 48 are in engagement with the locking holes 50 to lock the front cover 20, whereby the front cover 20 is prevented from opening accidentally. At this time, since the upper notched portion 31 is covered with the upper cover 29, the tape cassette 1 presents a good appearance.

On the other hand, when the tape cassette 1 is loaded onto the body of the video tape recorder, the front cover 20 and the inner cover 37 pivot upward as shown in FIG. 9, whereby the front and the back of the tape 9 are opened. That is, for example, when the tape cassette 1 is inserted into a cassette holder or the like disposed in the video tape recorder body, the right and left projections 52 formed on the cassette holder or the like are inserted from the slits 51 relatively in the direction of arrow "a" and urge tip end portions 49, as shown in FIG. 11. As a result, the leaf spring portions 49 are bent to the left in FIG. 11 against their spring forces, thus allowing the locking pawls 48 to be disengaged from the locking holes 50 to unlock the front cover 20.

Next, when the tape cassette 1 is moved downward in FIG. 11 and loaded in the cassette loading position, the front cover 20 is pushed up by a projection (not shown) formed on the video tape recorder body, so that as shown in FIG. 12 the front cover 20 is opened while twisting against the resilience of the torsion bar 26. On the other hand, when the front cover 20 pivots upward, the guide pins 41 of the inner cover 37 are guided by the guide grooves 44. Consequently, the guide pins 41 approach the pivot pins 22 during the section from the lower end portions up to the central portions 45 of the guide grooves 44, so that the inner cover 37 pivots counterclockwise about the pivot pins 38 in FIG. 8 with respect to the front cover 20. As a result, the space between the lower end portion 39 of the inner cover 37 and the lower end portion 34 of the front cover 20 becomes larger, thus preventing the front cover 20 and the inner cover 37 from contacting the tape 9 during their opening motion. After passing the central portion 45 of the guide grooves 44, the guide pins 41 gradually go away from the pivot pins 22 and the inner cover 37 pivots clockwise in FIG. 8 with respect to the front cover 20. And when the front cover 20 is fully open, as shown in FIG. 9, the inner cover 37 assumes a horizontal state and its lower end portion 39 contacts the inner surface of the lower end portion 34 of the front cover 20. Consequently, a wide space is ensured behind the tape 9, thus eliminating the inconvenience of having a tape loading guide (not shown) inserted from the notched portion 16 and the inner cover 37 strike against each other. Furthermore, since the inner cover 37 is opened and closed within the notched portion 16, the space for tape cassette loading within the video tape recorder body can be kept to a minimum space required.

On the other hand, along with the upward pivotal movement of the front cover 20, the upper cover 29 slides backward on the upper or first wall of the upper half 2. Therefore, the right and left end portions 30 of the torsion bar 26 do not pivot and only its central portion 28 is twisted by the upper end portion 25 of the front cover 20, so that an elastic energy which urges the upper cover 29 pivotally in a counterclockwise direction in FIG. 9 is accumulated. Consequently, the front cover 20 is urged in a clockwise direction in FIG. 9 by virtue of a reaction force acting on the upper cover 29, and when removing the tape cassette 1 from the video tape recorder body, the front cover 20 is closed by the force of the torsion bar 26.

When the tape cassette 1 is moved downward, as shown in FIG. 15, the unlocking pin 69 formed on the video tape recorder body is inserted through the hole 68 into the tape cassette 1 and urges the inclined surface 67 of the reel locking pawl 57, so that the first and second plate portions 58 and 59 move to the left in FIG. 15 together with the pawl portions 61, thus allowing the pawl portions 61 and the toothed portion 62 of the tape reels 7 and 8 to be disengaged from each other, whereby the tape reels 7 and 8 are unlocked.

When removing the tape cassette 1 from the video tape recorder body, the operational state of the front cover 20, inner cover 37, upper cover 29 and reel locking pawl 57 is completely reverse to the above-mentioned case, and the tape 9 passed along the opening portion 15 is sealed in the tape chamber 40 while being held between the front cover 20 on the one hand and the inner plate 35 and inner cover 37 on the other, therefore there is no fear of the tape 9 being damaged by dust or the like. In the removed state of the tape cassette 1, moreover, since the tape reels 7 and 8 are locked by the reel locking pawl 57 to prevent rotation of the reels in a direction that would loosen the tape in the opening 15, the tape 9 passed along the opening portion 15 will never be loosened by vibration or the like, and there does not occur such an inconvenience that the tape loading guide when inserted strikes against the tape 9.

Even if the reel locking pawl 57 is omitted, the tape 9 will never slacken to such an extent as causes a practical problem because it is held enclosed between the front cover 20 on the one hand and the inner plate 35 and inner cover 37 on the other. In this connection, a suitable cushioning material may be fixed on the inner wall surface of the front cover 20 and that of the inner cover 37 so that these cushioning materials lightly urge against the front and the back of the tape 9, the tape will not slacken at all even in the absence of the reel locking pawl 57.

An embodiment of the present invention has been described above, but the invention is not limited to the above-exemplified construction and various modifications may be made.

For example, although in the above embodiment the back of the tape 9 is covered with the inner plate 35 and the inner cover 37, there may be adopted a construction such that the inner plate 35 and the inner cover 37 are made integral with each other and the upper end portion of the inner plate 35 and that of the front cover 20 are hinged together to open and close the integral body of the inner plate 35 and the inner cover 37. Moreover, although in the above embodiment the inner cover 37 is made pivotable upward, it may be made movable in the longitudinal direction.

Therefore, the scope of the present invention is not limited to the precise embodiments and modifications described herein, but is defined solely by the appended claims.

What is claimed is:

1. A tape cassette comprising:
a housing containing reels on which a supply of tape is wound and having an opening along one side of the housing and a cutout in the bottom of the housing communicating with said opening along a portion of said opening, wherein said tape is guided between said reels in a path extending along said opening;
a front cover mounted on said housing and movable relative thereto between a closed position for covering said opening in front of said tape and an opened position for exposing said opening and the front of said tape; and
an inner cover movable with said front cover, said inner cover being positioned behind said tape to enclose said tape between said inner cover and said front cover when said front cover is in said closed position and the back of said tape being exposed when said front cover is in said opened position so that said tape can be engaged through said cutout for withdrawal of the tape through said opening.

2. A tape cassette according to claim 1, wherein said inner cover is hinged on said front cover for movement as said front cover moves between said closed position and said opened position.

3. A tape cassette according to claim 2, wherein said front cover includes a front plate for extending along said opening in front of said tape when said front cover is in said closed position and an inner plate for partially covering the back of said tape when said front cover is in said closed position and wherein said inner cover is hinged to said inner plate for covering the remainder of the back of said tape when said front cover is in said closed position.

4. A tape cassette according to claim 2, wherein said inner cover has a guide pin on one end thereof and said housing includes a guide groove having said guide pin disposed therein for guiding the movement of said inner cover as said front cover moves between said closed position and said opened position.

5. A tape cassette according to claim 4, wherein said front cover extends the full length of said one side of said housing and includes ears at the opposite ends thereof, said ears are pivoted to said housing on sides thereof adjacent to said one side of said housing, said inner cover extends the length of said cutout and has one of said guide pins at each end thereof, said housing has two inside walls at the ends of said cutout, and said inside walls each have a said guide groove therein.

6. A tape cassette according to claim 5, wherein said housing further includes a top wall and said cutout extends through said top and bottom walls, and said inner cover moves through said cutout in the top wall of the housing when said front cover moves from said closed position to said opened position.

7. A tape cassette according to claim 6, wherein said front cover further includes a cutout cover for covering said cutout in said top wall when said front cover is in said closed position, and said cutout cover is hinged on said front cover and slides on the top wall of said housing as said front cover moves between said closed position and said opened position.

8. A tape cassette according to claim 7, further comprising resilient torsion spring means hinging said cut-out cover to said front cover and by which said front cover is urged to its closed position.

9. A tape cassette according to claim 5, further comprising latching means on said housing for holding said front cover in said closed position said latching means being releasable for permitting use of the tape.

10. A tape cassette according to claim 1, further comprising reel locking means for preventing rotation of said reels in a direction that will loosen said tape in said opening, said reel locking means being releasable for permitting use of the tape.

11. A tape cassette according claim 10, wherein said reel locking means includes pawls for engaging saw-teeth on the peripheries of said reels, a leaf spring for urging said pawls against said saw-teeth and an inclined surface for cooperating with an unlocking means to move said pawls and permit rotation of said reels.

* * * * *